(12) United States Patent
Okuyama

(10) Patent No.: US 10,685,087 B2
(45) Date of Patent: Jun. 16, 2020

(54) MEDICAL IMAGE PROCESSING SYSTEM

(75) Inventor: Satoshi Okuyama, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 1034 days.

(21) Appl. No.: 13/575,636

(22) PCT Filed: Dec. 9, 2011

(86) PCT No.: PCT/JP2011/078515
§ 371 (c)(1),
(2), (4) Date: Jul. 27, 2012

(87) PCT Pub. No.: WO2012/086433
PCT Pub. Date: Jun. 28, 2012

(65) Prior Publication Data
US 2012/0323605 A1    Dec. 20, 2012

(30) Foreign Application Priority Data

Dec. 22, 2010 (JP) .................... 2010-285478

(51) Int. Cl.
*G06F 19/00* (2018.01)
*A61B 6/00* (2006.01)
(Continued)

(52) U.S. Cl.
CPC ........... *G06F 19/321* (2013.01); *A61B 6/463* (2013.01); *A61B 6/465* (2013.01); *A61B 6/563* (2013.01); *G16H 80/00* (2018.01); *A61B 6/03* (2013.01)

(58) Field of Classification Search
CPC ....... G06F 19/321; G06Q 50/24; A61B 19/56; A61B 6/463; A61B 6/465; A61B 6/563; A61B 6/03; G16H 80/00
(Continued)

(56) References Cited

U.S. PATENT DOCUMENTS

2003/0135481 A1* 7/2003 Helmes ................. G06Q 10/06
2005/0151731 A1* 7/2005 Matsumoto ........... G06F 9/5088
                                                              345/419
(Continued)

FOREIGN PATENT DOCUMENTS

CN         1702645 A      11/2005
JP      2002 140686         5/2002
(Continued)

OTHER PUBLICATIONS

International Search Report dated Mar. 13, 2012 in PCT/JP11/78515 Filed Dec. 9, 2011.

*Primary Examiner* — Joy Chng
(74) *Attorney, Agent, or Firm* — Oblon, McClelland, Maier & Neustadt, L.L.P.

(57) ABSTRACT

A server including an image storage, an image processor, a progress managing unit, and a UI controller. The image storage stores medical images of different body regions of a subject. The image processor receives requests related to each medical image from one of multiple clients and executes processing of the medical images. The progress managing unit creates progress information on the processing of each medical image based on the stage of the processing performed by the image processor on each of the multiple medical images, and centrally manages progress information for multiple medical images. In accordance with the processing stage indicated by the progress information, the UI controller generates display screen data which presents the processing status of the medical images of the corresponding body regions on multiple screen regions corresponding to multiple body regions and transmits the display screen data to either one of the multiple clients.

3 Claims, 9 Drawing Sheets

(51) Int. Cl.
*G16H 80/00* (2018.01)
*A61B 6/03* (2006.01)

(58) Field of Classification Search
USPC .......................................................... 705/2–3
See application file for complete search history.

(56) References Cited

U.S. PATENT DOCUMENTS

2008/0126982 A1* 5/2008 Sadikali ................ G06F 19/321
715/810
2011/0103660 A1* 5/2011 Butler ................... G06F 19/321
382/128

FOREIGN PATENT DOCUMENTS

| | | |
|---|---|---|
| JP | 2007 200340 | 8/2007 |
| JP | 2010 97323 | 4/2010 |
| JP | 2010 124937 | 6/2010 |
| JP | 2010 124943 | 6/2010 |
| JP | 2010 157184 | 7/2010 |

* cited by examiner

FIG. 8

| PROGRESS INFORMATION | | | | |
|---|---|---|---|---|
| OPERATOR | PROCESS-DETAILS | START-TIME | END-TIME | |
| OPERATOR Ub | PROCESSING T1 | 08/16 10:15 | 08/16 10:45 | ← R1a |
| OPERATOR Uc | PROCESSING T2 | 08/16 14:00 | 08/16 14:30 | ← R2a |
| OPERATOR Uc | PROCESSING T3 | 08/16 14:30 | — | ← R3a |
| E11 | E12 | E13 | E14 | |

D121

MEDICAL IMAGE PROCESSING SYSTEM

CROSS-REFERENCE TO RELATED APPLICATIONS

This application is based upon and claims the benefit of priority from Japanese Patent Application No. 2010-285478, filed Dec. 22, 2010; the entire contents of all of which are incorporated herein by reference.

FIELD

Embodiments of the present invention are related to technology that centrally manages processing of medical images in a server.

BACKGROUND

When using an image diagnosis device using CT (Computed Tomography), etc., for the purpose of reducing the exposure dose and shortening the imaging time, whole body imaging whereby images of the entire body are acquired through a single round of imaging is performed in some cases. When images of the entire body have been acquired through whole body imaging, processes such as radiogram interpretation for images of each region included in the captured medical images of the entire body may be divided among and performed by multiple operators.

Thin client systems that send processing requests from clients to a server via a network and then display the processing results from the server using the clients have started to be introduced as medical image processing systems. As a result of the introduction of such medical image processing systems, it has become possible for multiple operators to work in parallel to perform processing of medical images managed and stored on the server. Therefore, by using such a system, it becomes possible to divide and execute the processing of medical images among multiple operators.

When dividing the processing of medical images among multiple operators in this manner, as an example, for the images of each region, the primary physician sends a request to an operator specializing in the region so as to perform processing of the images of that region. Based on the request from the primary physician, each operator processes the images of the corresponding region and notifies the primary physician of the processing results. Moreover, there may be cases in which multiple operators perform the processing of a single region. In such a case, after completing their process, the operator receiving the processing request issues a new processing request to an operator in charge of the following process. Once all of the processing has been completed, the operator who performed the final processing notifies the primary physician of the processing results. When dividing and performing processing among multiple operators in this manner, it is important to monitor the work status of each operator in charge of the processing. However, in conventional systems, because the work status is monitored based on notifications of processing results from each operator, for example, it has been difficult for the primary physician or with each operator to easily confirm the work status of other operators.

The objective of the embodiment of the present invention is to make it possible to easily confirm the work status of each operator when dividing and performing the processing of medical images among multiple operators.

BRIEF DESCRIPTION OF THE DRAWINGS

FIG. 8 shows an example of the data structure of progress information according to the second embodiment.

DETAILED DESCRIPTION

To achieve the above objective, the first mode of the present embodiment is a medical image processing system including multiple clients and a server. The server includes an image storage, an image processor, a progress managing unit, and a UI controller. The image storage stores medical images of different body regions of a subject. The image processor receives requests related to each of the medical images from one of the multiple clients and executes processing of the medical images. The progress managing unit creates progress information on the processing of each medical image based on the stage of the processing performed by the image processor on each of the multiple medical images, and centrally manages the progress information of the multiple medical images. In accordance with the processing stage indicated by the progress information, the UI controller generates and transmits display screen data displaying the processing status of medical images of the corresponding body regions on multiple screen regions corresponding to multiple body regions to one of the multiple clients.

(First Embodiment)

Figure 1:
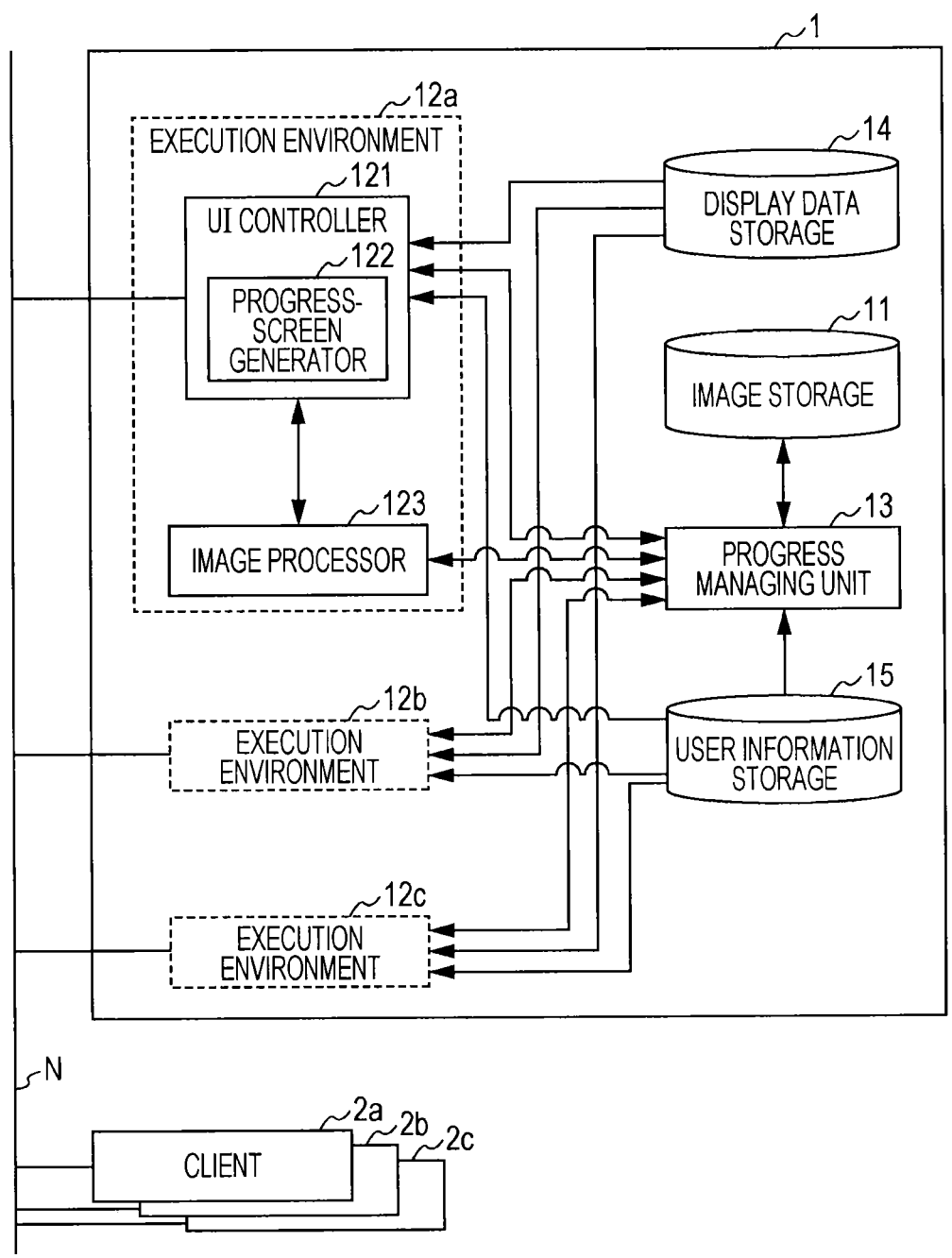
FIG. 1 is a block diagram of a medical image processing system according to the present embodiment.

The configuration of the medical image processing system according to the present embodiment is described with reference to FIG. 1. The medical image processing system according to the present embodiment is configured by connecting a server 1 with multiple clients via a network N. In the following, as shown in FIG. 1, descriptions shall refer to a configuration in which the server 1 and clients 2a-2c are connected via the network N.

The server 1 is configured to include an image storage 11, execution environments 12a-12c, a progress managing unit 13, a display data storage 14, and a user information storage 15.

Figure 2:
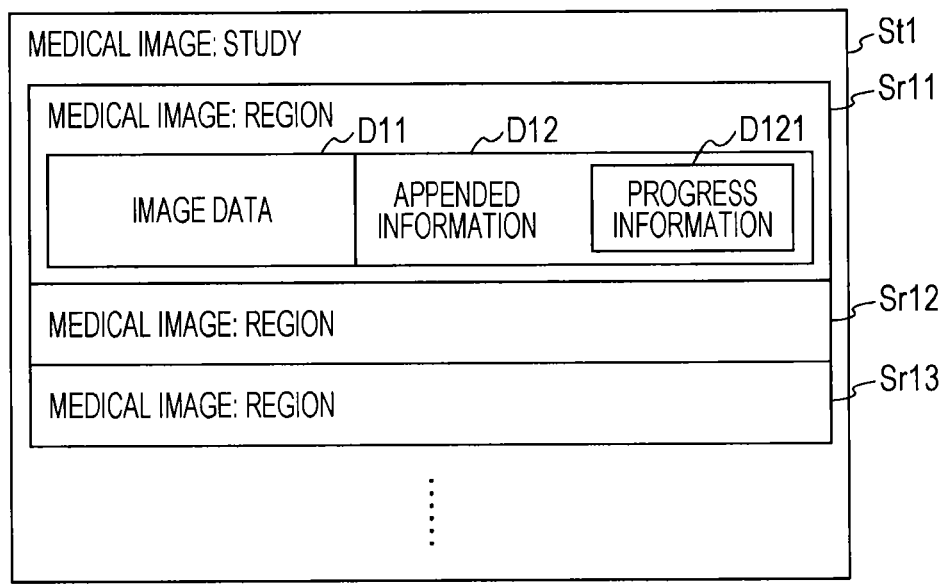
FIG. 2 shows an example of the data structure of medical images.

The image storage 11 is a storage region that stores medical images. The image storage 11 stores medical images captured using a medical imaging device such as a CT or MRI (Magnetic Resonance Imaging) device. The image storage 11 manages and stores these medical images with each study. Specifically, medical images of each region (hereinafter referred to as "series") captured with the medical imaging device are each associated with a study and stored in the image storage 11. For example, FIG. 2 shows an example of the data structure of medical images. As shown in FIG. 2, medical images Sr11-Sr13 for different series captured in a study St1, for example, are associated as medical images of the study St1. If, for example, whole body imaging has been performed, series-specific medical images of the head region, the chest region, and the abdominal region, etc. captured in the study are associated as a series of medical images, and the series-specific medical images are stored in a manner allowing them to be extracted. Moreover, the series-specific medical images Sr11-Sr13 are configured to include image data D11 and appended information D12. Moreover, in the appended information D12, progress information D121 for the progress managing unit 13 to manage the progress status of processing related to the series-specific medical images Sr11-Sr13 is appended by the progress managing unit 13. Details on the progress managing unit 13 and details on the progress information D121 are described later.

The execution environments 12a-12c are processing units for processing requests for processing of medical images and notifications of processing requests with each operator. The execution environments 12a-12c are each configure to include a UI controller 121, a progress-screen generator 122, and an image processor 123. Detailed operations of the UI controller 121, the progress-screen generator 122, and the image processor 123 are described later. Moreover, the execution environments 12a-12c are associated with the user information of each operator (Ua-Uc). The user information is created in advance with each operator and stored in the user information storage 15. The user information storage 15 is described later. In the following, the operator Ua, the operator Ub, and the operator Uc are described as those operating the client 2a, the client 2b, and the client 2c, respectively. In other words, processing requests from the client 2a are received and processed by the execution environment 12a. Moreover, the execution environment 12a transmits the results of the requested processing to the client 2a.

The user information storage 15 stores the user information related to the users of the medical image processing system according to the present embodiment. The ID and name, etc. of an operator are stored as the user information. Moreover, the user information is associated with one of the execution environments 12a-12c. For example, user information of the operator Ua is associated with the execution environment 12a. Based on this type of configuration, when the operator Ua logs into the server 1 via the client 2a, they are able to display messages for the operator Ua and the results of processing by other clients on the client 2a via the execution environment 12a.

The progress managing unit 13 receives requests related to processing of medical images stored in the image storage 11 from one operator together with information on the operator receiving the request, from the operator sending the request via one of the execution environments 12a-12c. The progress managing unit 13 notifies the execution environment of the operator receiving the request of the details of the request and also manages the progress status of that request. In the following, the series of operations of the progress managing unit 13 is divided into the triggers "Processing request", "Updating of progress information", and "Displaying of progress status" and described together with details operations of the UI controller 121, the progress-screen generator 122, and the image processor 123. Furthermore, in the following description, the client 2a is the request source and a processing request is sent to either one or both of the clients 2b and 2c.

(Processing Request)

First, using an example case in which the operator Ua requests processing for series-specific medical images Sr11-Sr13 captured in the study St1 to the operator Ub and the operator Uc, the operations of each configuration are described.

First, upon receiving an operation from the client 2a, the UI controller 121 requests the output of a list of studies from the progressing managing unit 13. Upon receiving this request, based on the series-specific medical images associated with each study and stored in the image storage 11, the progress managing unit 13 associates each study with the series corresponding to that study to create and output a list of studies to the UI controller 121. The UI controller 121 generates an operation screen in which each study included in the list of studies and the series for which medical images were acquired in those studies are displayed in a selectable manner, and displays the operation screen on a display unit of the client 2a. As a result, it becomes possible for the operator Ua to designate medical images of the series undergoing processing. It is advisable for operation screen formats and data of units such as buttons, images, and icons displayed on the operation screen used by the UI controller 121 to generate the operation screen to be stored in the display data storage 14 as display data. The display data storage 14 is described later.

The UI controller 121 receives a designation of the medical images of the series undergoing processing from the client 2a. The UI controller 121 reads out user information from the user information storage 15 and creates a list of operators. The UI controller 121 creates an operation screen in which each item of user information included in the list of operators is displayed in a selectable manner and displays the operation screen on the display unit of the client 2a. As a result, it becomes possible for the operator sending the request to designate the user information of the operator to receive the processing request. In this manner, the UI controller 121 receives medical images of the series undergoing processing and a designation of the user information of the operator to receive the processing request from the client 2a in a study-specific manner. The UI controller 121 associates and groups information indicating the selected series with the user information.

The UI controller 121 may operate so as to allow designation the medical images of multiple series as processing subjects. In this case, the UI controller 121 may operate so as to allow designation different request destinations for the medical images of each series.

The UI controller 121 outputs the associated group of information indicating the series and user information to the progress managing unit 13 together with information indicating the study. If medical images of multiple series have been selected, the UI controller 121 associates each associated group of information indicating the series and user information with a specific study and outputs them to the progress managing unit 13. This operation is described in detail using an example. For example, a series of medical images captured in the "study St1" includes a "head region medical image Sr11", a "chest region medical image Sr12", and an "abdominal region medical image Sr13". Let us suppose that based on an instruction from the client 2a, processing for the "head region medical image Sr11" is requested to the operator Ub, and processing for the "chest region medical image Sr12" is requested to the operator Uc. In this case, the UI controller 121 associates and groups information indicating the "head region medical image Sr11" with the user information of the operator Ub. Moreover, the UI controller 121 associates and groups information indicating the "chest region medical image Sr12" with the user information of the operator Uc. The UI controller 121 associates each associated group with information indicating the "study St1" and outputs them to the progressing managing unit 13.

Moreover, the UI controller 121 includes the progress-screen generator 122. Operations of the progress-screen generator 122 are described later together with operations related to the "displaying of progress status".

The display data storage 14 stores display data used to generate operation screens to be displayed by the UI controller 121 and the progress-screen generator 122 on the display unit of the client 2a. The display data include, for example, operation screen formats and data of units such as buttons, images, and icons to be displayed on the operation screen. Moreover, the display data storage 14 also stores display data of screens generated by the progress-screen generator 122 during the "displaying of progress status". This display data is described later together with the description of the progress-screen generator 122.

Figure 3:
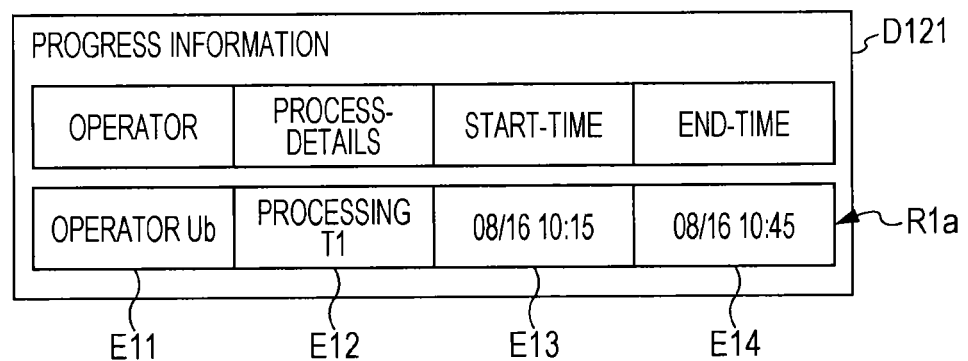
FIG. 3 shows an example of the data structure of progress information according to the first embodiment.

The progress managing unit 13 creates progress information D121 based on the user information included in each group received from the UI controller 121. The data structure of the progress information D121 is described with reference to FIG. 3. The progress information D121 is configured to include operator information E11, process-details information E12, start-time information E13, and end-time information E14. The operator information E11 indicates information of the operator receiving the processing request. The process-details information E12 indicates the details of the processing being requested (e.g., "radiogram interpretation" or "MPR (Multiplanar Reconstruction) processing", etc.). When the progress information is created, the operator information E11 and the process-details information E12 are input by the progress managing unit 13. The start-time information E13 indicates the start time at which the processing requested by the operator was started. The start-time information E13 is input by the progress managing unit 13 when processing by an operator has started (i.e., when the progress managing unit 13 receives a request from the image processor 123 so as to output the medical images of the series undergoing processing as the processing starts). The end-time information E14 indicates the end time at which the operator ends the requested processing. The end-time information E14 is input by the progress managing unit 13 when the processing by the operator has ended (i.e., when the progress managing unit 13 receives the medical images of the series after processing from the image processor 123).

The progress managing unit 13 manages the progress status of the processing of series-specific medical images by dividing it into, for example, processing stages F1-F5. Specifically, the progress managing unit 13 determines whether or not the progress information D121 has been generated in the appended information D12 and manages combinations of the information (E11-E14) input into the progress information D121 by associating them with one of the processing stages F1-F5. The following is a specific example. First, based on whether or not the progress information D121 has been appended to the appended information D12, the progress managing unit 13 determines whether or not processing for the medical images of the corresponding series has been requested. The progress managing unit 13 associates cases in which the progress information D121 does not have been appended to the appended information D12 with the progressing stage F1. In other words, the processing stage F1 indicates that processing of the medical images has not been requested. If progress information has been appended, the progress managing unit 13 manages combinations of parameters included in the progress information by associating them with each processing stage. For example, the progress managing unit 13 associates cases in which neither the start-time information E13 nor the end-time information E14 have been input with the processing stage F2. In other words, the processing stage F2 indicates that requested processing has not yet been executed (i.e., unprocessed). The progress managing unit 13 associates cases in which the start-time information E13 has been input and the end-time information E14 has not been input with the processing stage F3. In other words, the processing stage F3 indicates that requested processing is being executed. The progress managing unit 13 associates cases in which both the start-time information E13 and the end-time information E14 have been input with the processing stage F4. In other words, the processing stage F4 indicates that requested processing has been completed. If presenting a series that was not imaged in the study St1, it is advisable for the series to be associated with the processing stage F5 and presented in a manner distinguishable from the other processing stages. These associations are examples, and the combinations of the information E11-E14 and the combinations of the processing stages F1-F5 may be changed. Moreover, information may be added to the progress information, and processing stages may be added in accordance with such additions of information.

The progress managing unit 13 appends the created progress information D121 to the appended information D12 of the corresponding medical images. For example, let us suppose that the "processing T1 (e.g., MPR processing)" for the "head region medical image Sr11" imaged in the "study St1" has been requested to the "operator Ub". In this case, the progress managing unit 13 creates progress information in which the "operator Ub" has been input as the operator information E11 and the "processing T1" has been input as the "process-details information E12". The progress managing unit 13 appends the progress information that has been created to the appended information D12 of the "head region medical image Sr11" corresponding to the "study St1". The progress managing unit 13 also associates a series of the progress information D121 related to the study St1 with the user information of the operator Ua sending the request. As a result, the progress managing unit 13 identifies the operator Ua sending the request based on the user information associated with the progress information D121.

Next, to provide notification of processing requests for the series-specific medical images, the progress managing unit 13 identifies the execution environment of the operator sending the request based on the user information. For example, if the request source is the operator Ub, the progress managing unit 13 identifies the execution environment 12b corresponding to the operator Ub based on the user information. The progress managing unit 13 issues notification of the processing request related to the medical images to the identified execution environment 12b. As this time, based on, for example, the information "operator Ua" of the operator sending the request, the information "study St1" identifying the study, the medical image of the processing object "head region medical image Sr11", and the process details "processing T1", the progress managing unit 13 may create a message and notify the execution environment 12*b* that is the request destination. The progress managing unit 13 may also receive a message regarding the processing request via the execution environment 12*a* from the operator UA sending the request and notify to the execution environment 12*b* that is the request destination of this message. It is also possible to include information indicating contact information of the operator, such as an E-mail address, in the user information and cause the progress managing part 13 to deliver a request message to the contact destination.

In this way, with each medical image undergoing processing, the progress managing unit 13 creates and appends progress information, and notifies the execution environment of the operator receiving the processing request. As a result, it becomes possible for the operator receiving the request (the operator Ub) to confirm processing requests for medical images using the respective client that they operate (client 2*b*) via the corresponding execution environment (execution environment 12*b*). Subsequently, the progress managing unit 13 receives notification regarding the requested processing from each client requesting processing and updates the progress information appended to the medical images of the corresponding series. As a result, the progress managing unit 13 centrally manages the progress status of processing for series-specific medical images with each individual study. Details regarding the updating of progress information are described below.

(Updating of Progress Information)

Next, operations for updating the progress information D121 in accordance with the progress of the requested processing are described.

Let us suppose that the operator Ub operates the client 2*b* and starts processing the head region medical image Sr11 corresponding to the study St1 on the execution environment 12*b*. The UI controller 121 of the execution environment 12*b* receives an instruction with processing details for the head region medical image Sr11 from the client 2*b* and notifies the image processor 123 of the head region medical image Sr11 of the processing object and the details of the instructed processing. Moreover, the UI controller 121 acquires the results of processing of the head region medical image Sr11 from the image processor 123. The UI controller 121 displays the acquired processing results on the client 2*b*.

The image processor 123 is a processor that executes processing for medical images. The image processor 123 receives notification from the UI controller 121 and requests the progress managing unit 13 to output the head region medical image Sr11 of the processing object as designated in the notification. Upon receiving this request, the progress managing unit 13 reads out the head region medical image Sr11 corresponding to the study St1 from the image storage 11 and outputs the head region medical image Sr11 to the image processor 123. In relation to the head region medical image Sr11 received from the progress managing unit 13, the image processor 123 performs the processing instructed in receipt of the notification from the UI controller 121. When the processing of the head region medical image Sr11 is completed, the image processor 123 outputs the post-processing head region medical image Sr11 to the progress managing unit 13. Moreover, the image processor 123 outputs the results of the processing of the head region medical image Sr11 to the UI controller 121.

The progress managing unit 13 receives a request from the image processor 123 to output the head region medical image Sr11 corresponding to the study St1. The progress managing unit 13 reads out the head region medical image Sr11 corresponding to the study St1 from the image storage 11. Moreover, the progress managing unit 13 has a timekeeping means (not illustrated), and using the timekeeping means, identifies the time at which the request from the image processor 123 is received as the start time at which the processing is started. The progress managing unit 13 inputs the identified start time into the start-time information E13 of the progress information D121 appended to the head region medical image Sr11 that has been read out. As a result, the progress managing unit 13 confirms that the progress of the processing by the operator Ub for the head region medical image Sr11 has transitioned from the processing stage F2 (unprocessed) to the processing stage F3 (undergoing processing). In other words, if there is a request to present the processing stage at this point, the progress managing unit 13 provides notification that the current stage is the processing stage F3 (undergoing processing). The progress managing unit 13 outputs the head region medical image Sr11 to the image processor 123.

The progress managing unit 13 also receives the post-processing head region medical image Sr11 from the image processor 123. Using the timekeeping means, the progress managing unit 13 identifies the time at which the post-processing head region medical image Sr11 is received from the image processor 123 as the end time at which the processing is ended. The progress managing unit 13 inputs the identified end time into the end-time information E14 of the progress information D121 appended to the post-processing head region medical image Sr11. As a result, the progress managing unit 13 confirms that the progress of the processing by the operator Ub for the head region medical image Sr11 has transitioned from the processing stage F3 (undergoing processing) to the processing stage F4 (processing complete). In other words, if there is a request to present the processing stage at this point, the progress managing unit 13 provides notification that the current stage is the processing stage F4 (processing complete). The progress managing unit 13 stores the head-region medical image Sr11 in the image storage 11.

Of the series-specific medical images corresponding to the study St1, the progress managing unit 13 confirms the progress information of medical images (to which progress information has been appended) for which processing has been requested. For all of the medical images for which processing has been requested, if the processing is complete, the progress managing unit 13 reads out the user information of the operator Ua, who is the request source associated with the progress information D121. The progress managing unit 13 identifies the execution environment 12*a* corresponding to the operator Ua based on the user information, and notifies the execution environment 12*a* that the requested processing for the medical images related to the study St1 has been completed. In this way, the progress managing unit 13 centrally manages processing for series-specific medical images with each individual study.

(Displaying of Progress Status)

Figure 4:
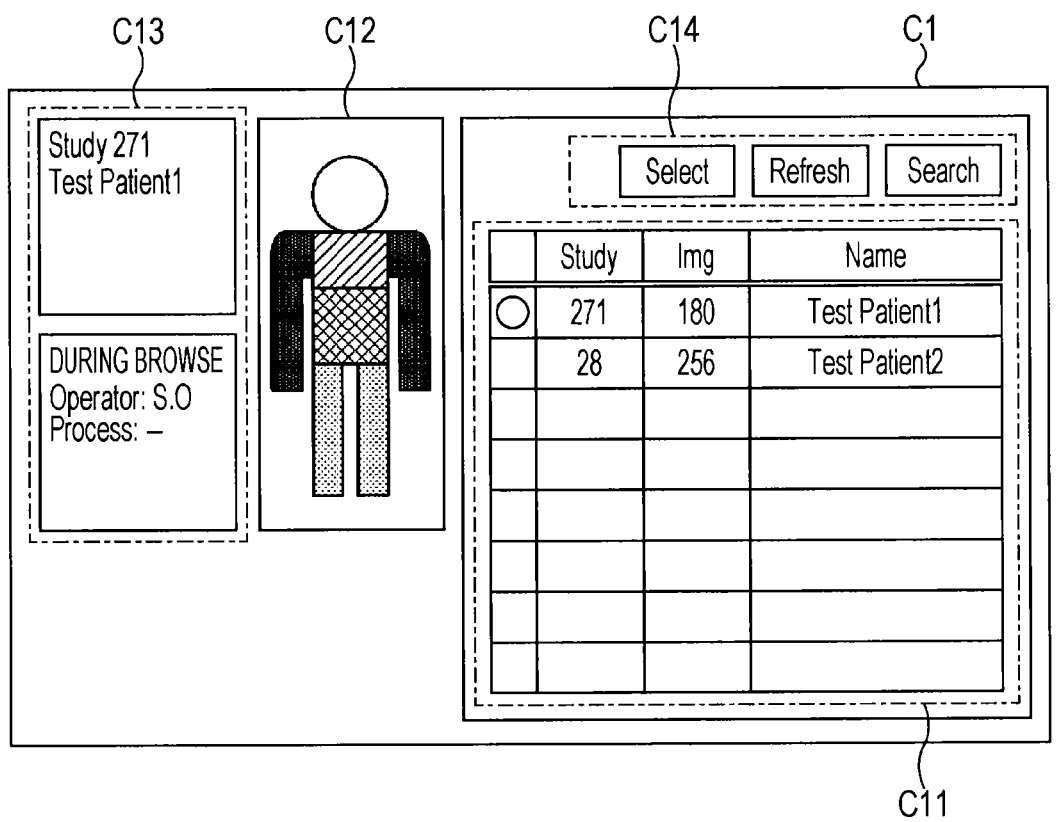
FIG. 4 shows an example of an operation screen of the medical image processing system according to the present embodiment.

Next, operations of each configuration related to the displaying of progress status are described together with the configurations of screens that are displayed, with reference to FIG. 4. FIG. 4 shows an example of an operation screen of the medical image processing system according to the present embodiment.

An operation screen C1 is a screen for confirming, with each study, processing requests for series-specific medical images associated with the study as well as the progress status of requested processing. The operation screen C1 is divided into screen regions and includes a study-list display unit C11, a progress-status display unit C12, a study-information display unit C13, and an operation means C14. The UI controller 121 reads out display data stored in the display data storage 14 and generates the operation screen C1. Moreover, the UI controller 121 generates the study-list display unit C11, the study-information display unit C13, and the operation means C14 and further displays them at prescribed positions on the operation screen C1. Moreover, the UI controller 121 causes the progress-screen generator 122 to generate the progress-status display unit C12 and displays the progress-status display unit C12 at a prescribed position on the operation screen C1. In the following, the configurations of the study-list display unit C11, the progress-status display unit C12, the study-information display unit C13, and the operation means C14 as well as operations related to the generation of each unit are each described.

The study-list display unit C11 is a region for displaying a list of studies with which medical images stored in the image storage 11 have been associated. The UI controller 121 acquires the list of studies from the progress managing unit 13 and generates the study-list display unit C11, which displays each study included in the list of studies in a manner allowing them to be selected by use of, for example, a marker or a pointer. The UI controller 121 displays the generated study-list display unit C11 at a prescribed position on the operation screen C1.

The progress-status display unit C12 is a region for displaying the progress status of processing for series-specific medical images associated with a study selected in the study-list display unit C11. The progress-status display unit C12 is generated by the progress-screen generator 122. Operations of the progress-screen generator 122 are described later.

Figure 5:
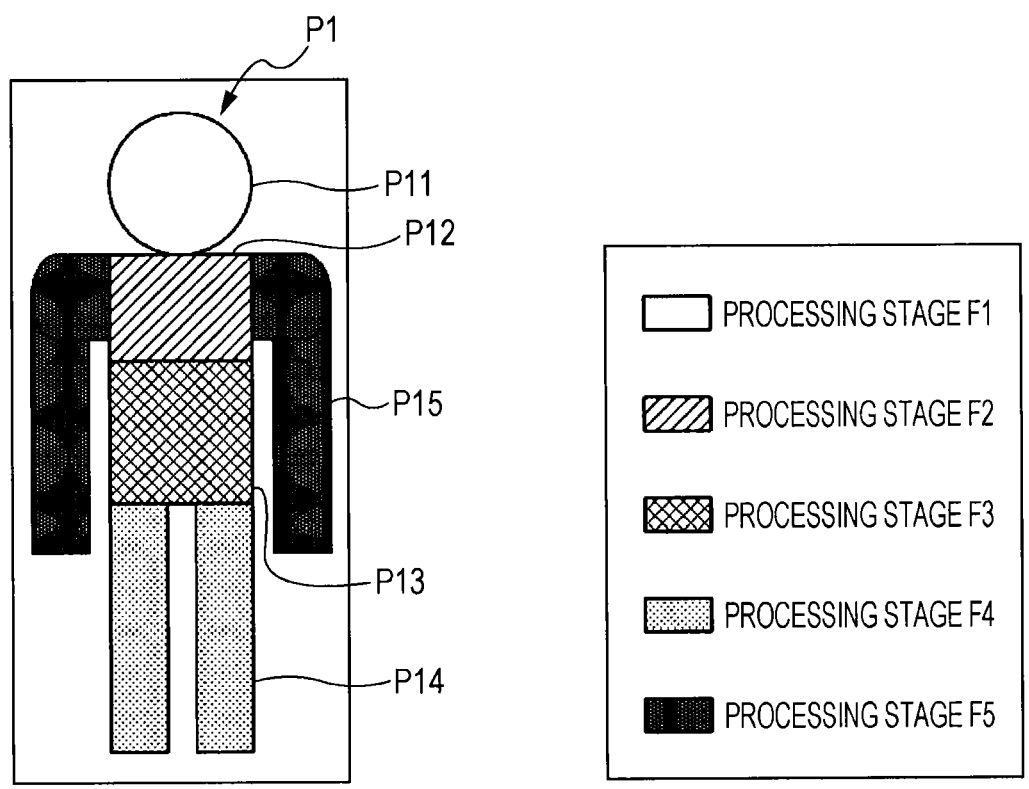
FIG. 5 shows an example of an operation screen of the medical image processing system according to the present embodiment.

Here, we shall refer to FIG. 5. FIG. 5 shows the detailed configuration of the progress-status display unit C12 of FIG. 4. As shown in FIG. 5, the progress-status display unit C12 includes a display region P1 that resembles a body. The display region P1 is configured by including the partial regions P11-P15 corresponding to the body regions. The partial regions P11-P15 are associated with the medical images of each series corresponding to the study selected in the study-list display unit C11. For example, the partial region P11 corresponds to the head region and is associated with medical images of the head region. Similarly, the partial region P12, the partial region P13, the partial region P14, and the partial region P15 are respectively associated with the chest region, the abdominal region, the legs, and the arms. Moreover, in accordance with the progress status of processing for the associated medical images, the partial regions P11-P15 are displayed with color-coded as shown in FIG. 5 by the progress-screen generator 122. For example, the partial region P11 shows that the progress status of processing for medical images of the head region is at the processing stage F1.

Data for generating the display region P1 and the partial regions P11-P15 are stored as display data in the display data storage 14. Moreover, color data for color-coding the partial regions P11-P15, as well as associations between each color and the processing stages F1-F5, are stored as display data in the display data storage 14.

Operations of the progress-screen generator 122 related to the generation of the progress-status display unit C12 are described. When a study displayed on the study-list display unit C11 is selected by an operator, the progress-screen generator 122 first reads out the display data of the display region P1 and the partial regions P11-P15 from the display data storage 14. The progress-screen generator 122 generates the progress-status display unit C12 based on the display data that have been read out.

Moreover, the progress-screen generator 122 requests the progress managing unit 13 to output the appended information D12 corresponding to the study selected on the study-list display unit C11. Upon receiving this request, the progress managing unit 13 reads out the series-specific medical images associated with the designated study from the image storage 11. The progress managing unit 13 outputs the appended information D12 of the medical images that have been read out to the progress-screen generator 122 with each individual series. The progress-screen generator 122 associates the appended information D12 received with each individual series from the progress managing unit 13 with the partial region corresponding to the series. For example, let us suppose that in the study St1, the head region medical image Sr11, the chest region medical image Sr12, the abdominal region medical image Sr13, and the leg medical image Sr14 were captured. In this case, the progress-screen generator 122 associates the appended information D12 of the head region medical image Sr11 with the partial region P11 corresponding to the head region. Similarly, the progress-screen generator 122 associates the appended information D12 of the chest region medical image Sr12 with the partial region P12, the appended information D12 of the abdominal region medical image Sr13 with the partial region P13, and the appended information D12 of the leg medical image Sr14 with the partial region P14.

Next, the progress-screen generator 122 reads out the progress information D121 from the appended information D12 associated with the partial region. In accordance with the processing stage indicated by the progress information D121, the progress-screen generator 122 reads out the data of the color corresponding to the processing stage from the display data storage 14. Based on the color data that have been read out, the progress-screen generator 122 displays the corresponding partial region in that color. As a result, as shown in FIG. 5, the partial region P11 indicating the head region, for example, is displayed in the progress-status display unit C12 in the color corresponding to the processing stage F1. Based on this display, it becomes possible for the operator to confirm that the progress status of processing for the head region medical image Sr11 of the study St1 is at the processing stage F1. Similarly, the progress-screen generator 122 color-codes and displays the partial regions P12-P14 based on the progress information of the corresponding medical images. Moreover, the progress-screen generator 122 displays the partial region P15 that is not associated with any appended information D12 in the color corresponding to the processing stage F5. By displaying each partial region in this manner, in becomes possible for the operator to easily determine the series for which medical images have been captured as well as the progress status of processing for those series. In the above descriptions, a method of identification based on color has been described, but there are no limitations to the method as long as it is possible to determine the progress status of processing for the medical images of each series. For example, different icons may be displayed in each partial region, or character information may be displayed.

Here, we shall refer to FIG. 4. The study-information display unit C13 is a region for displaying detailed information of medical images associated with a partial region selected in the progress-status display unit C12. When a partial region on the progress-status display unit C12 is selected, the UI controller 121 acquires appended information associated with the partial region from the progress-screen generator 122. The UI controller 121 reads out information such as patient name, etc. from the appended information and generates the study-information display unit C13 based on this information. Moreover, the UI controller 121 reads out progress information from the appended information and displays the processing details input in the progress information and information on the operator executing the processing, etc. on the study-information display unit C13. The UI controller 121 displays the generated study-information display unit C13 at a predetermined position on the operation screen C1.

The operation means C14 is a region for displaying buttons, etc. for performing operations on the operation screen C1. The UI controller 121 generates the operation means C14 in which, for example, a Select button, an Update button, and/or a Search button, etc. are displayed. The Select button is a button for displaying the details of a study selected in the study-list display unit C11. The Update button is a button for reacquiring the list of studies and updating the list of studies displayed in the study-list display unit C11. The Search button is a button for displaying a search means for searching for studies corresponding to desired conditions. The search means is a conventional technology, and therefore, detailed descriptions are omitted. The UI controller 121 displays the generated operation means C14 at a prescribed position on the operation screen C1.

By displaying the operation screen C1 as described above, it becomes possible to easily confirm, with each individual study, the status of processing for medical images of each series as well as the details of such processing.

Figure 6:
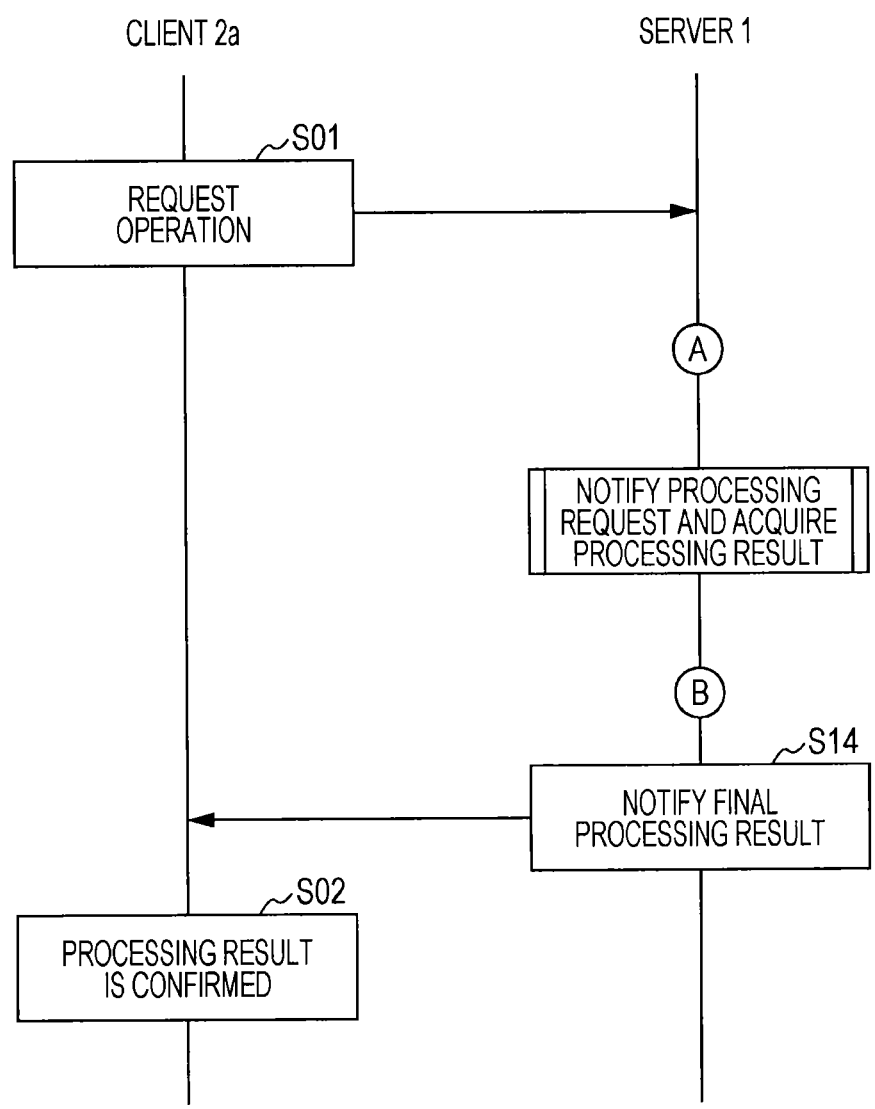
FIG. 6 is an explanatory diagram of the flow of a series of processes of the medical image processing system according to the present embodiment.
Figure 7:
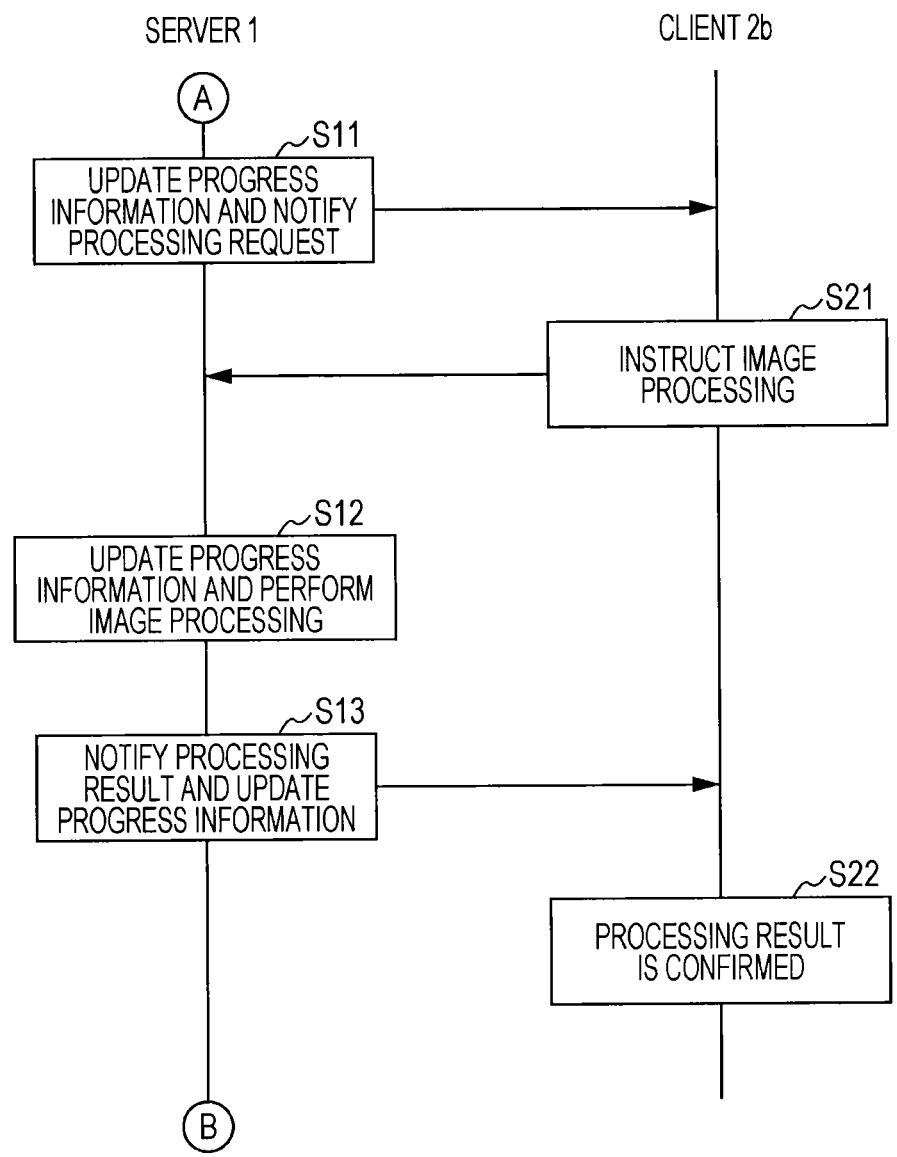
FIG. 7 is a diagram showing the flow of processes between the server and a client of the medical image processing system according to the first embodiment.

Next, a series of operations of the medical image processing system according to the present embodiment is described with reference to FIG. 6 and FIG. 7. FIG. 6 is a flowchart showing a series of operations related to confirming processing requests and processing results. FIG. 7 is a flowchart showing operations related to the acquisition of notifications of request details as well as processing results based on requests. The following describes an example in which the operator Ua operating the client 2a requests the "operator Ub" to perform the "processing T1" for the "head region medical image Sr11" captured in the "study St1".
(Step S01)
First, we shall refer to FIG. 6. Upon receiving an operation from the client 2a, the UI controller 121 requests the progress managing unit 13 to output a list of studies. Upon receiving this request, based on series-specific medical images that have been associated with each individual study and stored in the image storage 11, the progress managing unit 13 associates each study with the series that were subject to that study to create the list of studies and output it to the UI controller 121. The UI controller 121 generates an operation screen in which each study included in the list of studies as well as the series for which medical images were acquired in those studies are displayed in a selectable manner, and displays this operation screen in the display unit of the client 2a. As a result, it becomes possible for the operator Ua to designate medical images of the series object to processing with each individual study.

The UI controller 121 receives a designation of the medical images of the series object to processing from the client 2a. The UI controller 121 reads out user information from the user information storage 15 and creates a list of operators. The UI controller 121 generates an operation screen in which each item of user information included in the list of operators is displayed in a selectable manner, and displays this operation screen in the display unit of the client 2a. As a result, it becomes possible for the operator Ua sending the request to designate the user information of the operator Ub who is receiving the processing request. In this way, with each individual study, the UI controller 121 receives from the client 2a designations of the medical images of the series object to processing as well as the user information of the operator receiving the processing request. The UI controller 121 groups and associates information indicating the selected series with the user information.

The UI controller 121 outputs the associated group of the information indicating the series and the user information to the progress managing unit 13 together with information indicating the study. If medical images of multiple series have been selected, with each individual study, the UI controller 121 associates each associated group of the information indicating the series and the user information and outputs them to the progress managing unit 13.
(Step S11)
Here, we shall refer to FIG. 7. The progress managing unit 13 creates the progress information D121 based on the user information included in each group received from the UI controller 121 of the execution environment 12a. In this case, the progress managing unit 13 creates progress information in which "operator Ub" has been input in the operator information E11 and "processing T1" has been input in the process-details information E12. The progress managing unit 13 appends the created progress information D121 to the appended information D12 of the corresponding medical images. Moreover, the progress managing unit 13 associates a series of the progress information D121 related to the study St1 with the user information of the operator Ua, who is the request source. If the progress status is checked at this time, on the progress-status display unit C12, the partial region P11 corresponding to the head region is displayed in a color corresponding to the processing stage F2 (unprocessed).

Next, the progress managing unit 13 identifies the execution environment 12b of the operator Ub, who is the request destination, based on the user information. The progress managing unit 13 notifies the identified execution environment 12b of the processing request related to the medical images.
(Step S21)
Upon receiving this request, the operator Ub operates the client 2b and, in the execution environment 12b, provides instructions regarding the details of the processing T1 for the head region medical image Sr11 corresponding to the study St1.
(Step S12)
The UI controller 121 of the execution environment 12b receives the instructions regarding the details of the processing T1 for the head region medical image Sr11 from the client 2b and notifies the image processor 123 of the head region medical image Sr11 of the processing object as well as the instructed processing details.

The image processor 123 of the execution environment 12b is a processor that executes processing of medical images. The image processor 123 receives the notification from the UI controller 121 and requests the progress managing unit 13 to output the head region medical image Sr11 that is the processing object and was designated in the notification.

Upon receiving this request, the progress managing unit 13 reads out the head region medical image Sr11 corresponding to the study St1 from the image storage 11.

Moreover, the progress managing unit 13 identifies the time at which the request is received from the image processor 123 as the start time. The progress managing unit 13 inputs the identified start time in the start-time information E13 of the progress information D121 appended to the head region medical image Sr11 that has been read out. In this way, the progress managing unit 13 recognizes that the progress of the processing performed by the operator Ub for the head region medical image Sr11 has transitioned from the processing stage F2 (unprocessed) to the processing stage F3 (undergoing processing).

The progress managing unit 13 outputs the head region medical image Sr11 that has been read out to the image processor 123 of the execution environment 12b. In relation to the head region medical image Sr11 received from the progress managing unit 13, the image processor 123 performs the processing instructed in the notification from the UI controller 121. If the progress status is checked at this time, on the progress-status display unit C12, the partial region P11 corresponding to the head region is displayed in a color corresponding to the processing stage F3 (undergoing processing).
(Step S13, Step S22)

When the processing of the head region medical image Sr11 is complete, the image processor 123 of the execution environment 12b outputs the post-processing head region medical image Sr11 to the progress managing unit 13. Moreover, the progress managing unit 13 identifies the time at which the post-processing head region medical image Sr11 is received from the image processor 123 as the end time. The progress managing unit 13 inputs the identified end time in the end-time information E14 of the progress information D121 appended to the post-processing head region medical image Sr11. In this way, the progress managing unit 13 recognizes that the progress of the processing performed by the operator Ub for the head region medical image Sr11 has transitioned from the processing stage F3 (undergoing processing) to the processing stage F4 (processing complete). The progress managing unit 13 stores the head region medical image Sr11 in the image storage 11. Moreover, the image processor 123 outputs the results of the processing performed on the head region medical image Sr11 to the UI controller 121. The UI controller 121 displays the acquired processing results on the client 2b (Step S13). As a result, the results of the image processing are displayed on the client 2b that is operated by the operator Ub (Step S22). If the progress status is checked at this time, on the progress-status display unit C12, the partial region P11 corresponding to the head region is displayed in a color corresponding to the processing stage F4 (processing complete).
(Step S14, Step S02)

Here, we shall refer to FIG. 6. From among the series-specific medical images corresponding to the study St1, the progress managing unit 13 checks the progress information of the medical images for which processing has been requested. If processing has been completed for all of the medical images for which processing has been requested, the progress managing unit 13 reads out the user information of the operator Ua, who is the request source associated with the progress information D121. The progress managing unit 13 identifies the execution environment 12a corresponding to the operator Ua based on the user information and notifies the execution environment 12a that the processing requested for the medical images related to the study St1 has been completed (Step S14). In this way, the completion of the requested processing is notified on the client 2a that is operated by the operator Ua (Step S02).

As described above, according to the medical image processing system of the present embodiment, depending on the progress status of processing for series-specific medical images, the progress information appended to the medical images is updated. In this process, based on the progress information, it becomes possible to display the progress status of the processing performed on series-specific medical images on a screen in relation to each individual study. By using this type of configuration, when dividing and performing the processing of series-specific medical images among multiple operators, it becomes possible to easily confirm the work status of each operator with each individual study.
(Second Embodiment)

In the medical image processing system of the first embodiment, cases were described in which, with each set of series-specific medical images, processing is executed by a single operator. The medical image processing system of the second embodiment includes cases in which multiple operators perform sequential processing on a single medical image. In such a case, the medical image processing system manages the progress status of each process being performed on the medical image. In the following, the medical image processing system of the present embodiment is described, with a focus on parts that are different from the medical image processing system of the first embodiment.

First, the structure of the progress information according to the present embodiment is described with reference to FIG. 8. FIG. 8 shows an example of the data structure of progress information according to a variation. In the progress information D121 according to the variation, the operator information E11, the process-details information E12, the start-time information E13, and the end-time information E14 are included in a single row, and one or more instances of such rows are included. As shown in R1a-R3a of FIG. 8, the progress managing unit 13 creates and manages this row with each process performed on a medical image to which the progress information D121 has been appended. In other words, by creating and managing this row with each process, the progress managing unit 13 manages the progress status of each process.

The progress managing unit 13 associates combinations of the information (C11-C14) input into each row with one of the processing stages F1-F5 and manages them with each row (i.e., with each process). The associations between the combinations of the information (C11-C14) with the processing stages F1-F5 are the same as those in the First Embodiment. For example, the row R1a indicates the progress information of the "processing T1" performed by the "operator Ub". The row R2a indicates the progress information of the "processing T2" performed by the "operator Uc". Because information has been input in the end-time information E14 of the rows R1a and R2a, this indicates that the processes have been completed. Moreover, the row R3a indicates the progress information of the "processing T3" performed by the "operator Uc". In the row R3a, because the start-time information E13 has been input and the end-time information E14 has not been input, this indicates that the processing is still taking place. In this way, for multiple processes performed on a single medical image, the progress managing unit 13 creates a row with each process in the progress information D121 corresponding to the medical image. Moreover, by inputting information in each corresponding row in accordance with the progress status of each process, the progress managing unit 13 manages the progress status of each of these processes. The trigger for creating each row and the trigger for updating the information (C11-C14) included in each row are the same as the triggers for creating and updating the progress information D121 according to the First Embodiment.

It is advisable that the progress-screen generator 122 according to the present embodiment generates the progress-status display unit C12 based on one of the rows R1a-R3a included in the progress information D121. As an example, the progress-screen generator 122 generates the progress-status display unit C12 based on the newest row R3a from among the rows R1a-R3a.

The progress-screen generator 122 may display the rows R1a-R3a included in the progress information D121 in a referable manner as history information. For example, from one of the clients 2a-2c, the progress-screen generator 122 receives a selection of one of the partial regions P11-P15 displayed in the progress-status display unit C12. At this time, the progress-screen generator 122 reads out the progress information D121 from the appended information D12 associated with the selected partial region. The progress-screen generator 122 creates the history information based on the rows R1a-R3a include in the progress information D121 that has been read out. The progress-screen generator 122 outputs the created history information to the UI controller 121. It is advisable that the UI controller 121 displays the history information as a dialog on the operation screen C1, for example.

Figure 9:
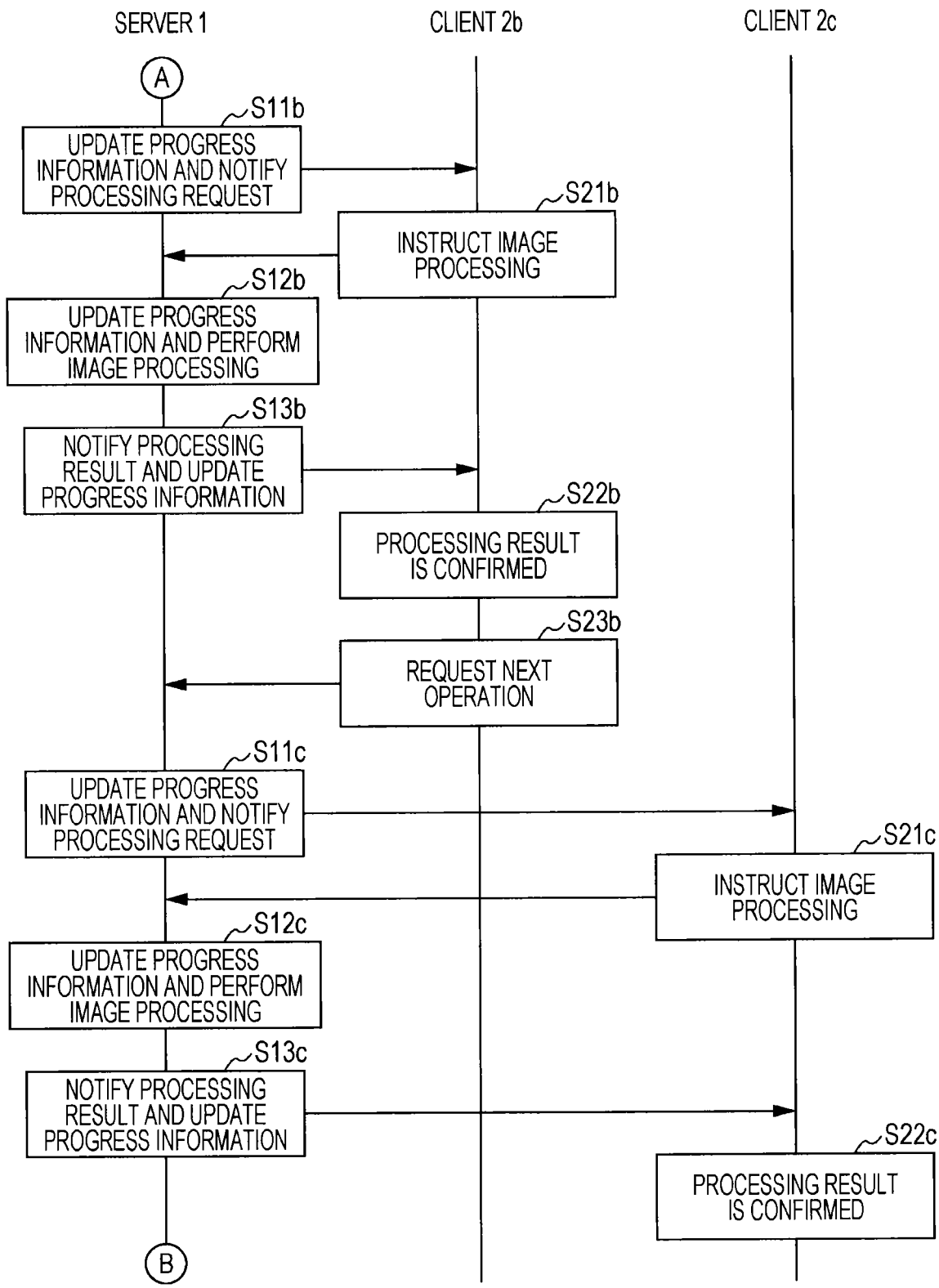
FIG. 9 is a diagram showing the flow of processes between the server and a client of the medical image processing system according to the second embodiment.

Next, a series of operations of the medical image processing system according to the present embodiment is described with reference to FIG. 6 and FIG. 9. FIG. 6 is a flowchart showing a series of operations related to confirming a processing request and processing results. FIG. 9 is a flowchart showing operations related to the acquisition of processing results based on a notification of request details and a request. The following describes an example case in which, based on a request from the operator Ua operating the client 2a, the "operator Ub" executes the "processing T1" on the "head region medical image Sr11" and the "operator Uc" executes the "processing T2" on the "head region medical image Sr11".

(Step S01)

First, we shall refer to FIG. 6. Upon receiving an operation from the client 2a, the UI controller 121 requests the progress managing unit 13 to output a list of studies. Upon receiving this request, based on series-specific medical images that have been associated with a specific study and stored in the image storage 11, the progress managing unit 13 associates each study with the series that are the subject of that study to create and output the list of studies to the UI controller 121. The UI controller 121 generates an operation screen in which each study included in the list of studies as well as the series for which medical images were acquired in the studies are displayed in a selectable manner, and displays this operation screen in the display unit of the client 2a. As a result, with each individual study, it becomes possible for the operator Ua to designate medical images of the series object to processing.

The UI controller 121 receives a designation of medical images of the series object to processing from the client 2a. The UI controller 121 reads out user information from the user information storage 15 and creates a list of operators. The UI controller 121 generates an operation screen in which each item of user information included in the list of operators is displayed in a selectable manner, and displays this operation screen in the display unit of the client 2a. As a result, it becomes possible for the operator sending the request to designate the user information of the operator receiving the processing request. In this way, with each individual study, the UI controller 121 receives from the client 2a medical images of the series object to processing as well as the designation of the user information of the operator receiving the processing request. The UI controller 121 groups and associates the information indicating the selected series with the user information.

The UI controller 121 outputs the associated groups of the information indicating the series and the user information to the progress managing unit 13 together with information indicating the study. If medical images of multiple series have been selected, the UI controller 121 associates each associated group of the information indicating the series and the user information with an individual study and outputs them to the progress managing unit 13.

(Step S11b)

Here, we shall refer to FIG. 9. The progress managing unit 13 creates the row R1a based on the user information included in each group received from the UI controller 121 of the execution environment 12a, and creates the progress information D121 that includes the row R1a. In this case, the progress managing unit 13 creates the progress information D121 that includes the row R1a, in which the "operator Ub" has been input in the operator information E11 and the "processing T1" has been input in the process-details information E12. The progress managing unit 13 appends the created progress information D121 to the appended information D12 of the corresponding medical image. Moreover, the progress managing unit 13 associates a series of the progress information D121 related to the study St1 with the user information of the operator Ua, who is the request source. If the progress status is checked at this time, on the progress-status display unit C12, the partial region P11 corresponding to the head region is displayed in a color corresponding to the processing stage F2 (unprocessed) to indicate the progress status of the processing T1.

Next, the progress managing unit 13 identifies the execution environment 12b of the operator Ub, who is the request destination, based on the user information. The progress managing unit 13 notifies the identified execution environment 12b of the processing request related to the medical images.

(Step S21b)

Upon receiving this request, the operator Ub operates the client 2b and, in the execution environment 12b, issues instructions related to the details of the processing T1 for the head region medical image Sr11 corresponding to the study St1.

(Step S12b)

The UI controller 121 of the execution environment 12b receives from the client 2b the instructions related to the details of the processing T1 for the head region medical image Sr11, and notifies the image processor 123 of the head region medical image Sr11 of the processing object as well as the instructed processing details. The image processor 123 receives the notification from the UI controller 121 and requests the progress managing unit 13 to output the head region medical image Sr11 that has been designated in the notification and is the processing object.

Upon receiving this request, the progress managing unit 13 reads out the head region medical image Sr11 corresponding to the study St1 from the image storage 11. Moreover, the progress managing unit 13 identifies the time at which the request is received from the image processor 123 as the start time. The progress managing unit 13 inputs the identified start time into the start-time information E13 of the row R1a in the progress information D121 appended to the head region medical image Sr11 that has been read out. As a result, the progress managing unit 13 recognizes that the progress of the processing performed by the operator Ub on the head region medical image Sr11 has transitioned from the processing stage F2 (unprocessed) to the processing stage F3 (undergoing processing).

The progress managing unit 13 outputs the head region medical image Sr11 that has been read out to the image processor 123 of the execution environment 12b. In relation to the head region medical image Sr11 received from the progress managing unit 13, the image processor 123 performs the processing instructed in the notification from the UI controller 121. If the progress status is checked at this time, on the progress-status display unit C12, the partial region P11 corresponding to the head region is displayed in a color corresponding to the processing stage F3 (undergoing processing) to indicate the progress status of the processing T1.
(Step S13b, Step S22b)

When the processing of the head region medical image Sr11 is complete, the image processor 123 of the execution environment 12b outputs the post-processing head region medical image Sr11 to the progress managing unit 13. Moreover, the progress managing unit 13 identifies the time at which the post-processing head region medical image Sr11 is received as the end time. The progress managing unit 13 inputs the identified end time into the end-time information E14 of the row R1a in the progress information D121 appended to the post-processing head region medical image Sr11. As a result, the progress managing unit 13 recognizes that the progress of the processing performed by the operator Ub on the head region medical image Sr11 has transitioned from the processing stage F3 (undergoing processing) to the processing stage F4 (processing complete). The progress managing unit 13 stores the results of the processing performed on the head region medical image Sr11 in the image storage 11. Moreover, the image processor 123 outputs the results of the processing performed on the head region medical image Sr11 to the UI controller 121. The UI controller 121 displays the acquired processing results on the client 2b (Step S13b). As a result, the results of the processing T1 are displayed on the client 2b that is operated by the operator Ub (Step S22b). If the progress status is checked at this time, on the progress-status display unit C12, the partial region P11 corresponding to the head region is displayed in a color corresponding to the processing stage F4 (processing complete) to indicate the progress status of the processing T1.
(Step S23b)

The operator Ub operates the client 2b and requests the operator Uc to perform the subsequent process (processing T2) on the head region medical image Sr11. The processes related to the request regarding the processing T2 from the operator Ub to the operator Uc are the same as the operations related to the request regarding the processing T1 from the operator Ua to the operator Uc described in Step S01.
(Step S11c)

The progress managing unit 13 creates the row R2a based on the user information included in each group received from the UI controller 121 of the execution environment 12b and adds it to the progress information D121 corresponding to the head region medical image Sr11. In this case, the progress managing unit 13 adds to the row R2a, in which the "operator Uc" has been input in the operator information E11 and the "processing T2" has been input in the process-details information E12, to the progress information D121. If the progress status is checked at this time, on the progress-status display unit C12, the partial region P11 corresponding to the head region is displayed in a color corresponding to the processing stage F2 (unprocessed) to indicate the progress status of the processing T2.

Next, the progress managing unit 13 identifies the execution environment 12c of the operator Uc, who is the request destination, based on the user information. The progress managing unit 13 notifies the identified execution environment 12c of the processing request related to the medical image.
(Step S21c)

Upon receiving this request, the operator Ub operates the client 2c and, in the execution environment 12c, issues instructions regarding the details of the processing T2 for the head region medical image Sr11 corresponding to the study St1.
(Step S12c)

The UI controller 121 of the execution environment 12c receives the instructions regarding the details of the processing T2 for the head region medical image Sr11 from the client 2c, and notifies the image processor 123 of the head region medical image Sr11 of the processing object as well as the instructed processing details. The image processor 123 receives the notification from the UI controller 121 and requests the progress managing unit 13 to output the head region medical image Sr11 that has been designated in the notification and is object to processing.

Upon receiving this request, the progress managing unit 13 reads out the head region medical image Sr11 corresponding to the study St1 from the image storage 11. Moreover, the progress managing unit 13 identifies the time at which the request is received from the image processor 123 as the start time. The progress managing unit 13 inputs the time at which the processing starts (i.e., the time at which the request is received) into the start-time information E13 of the row R2a in the progress information D121 appended to the head region medical image Sr11 that has been read out. As a result, the progress managing unit 13 recognizes that the progress of the processing performed by the operator Uc on the head region medical image Sr11 has transitioned from the processing stage F2 (unprocessed) to the processing stage F3 (undergoing processing).

The progress managing unit 13 outputs the head region medical image Sr11 that has been read out to the image processor 123 of the execution environment 12c. In relation to the head region medical image Sr11 received from the progress managing unit 13, the image processor 123 performs the processing instructed in the notification from the UI controller 121. If the progress status is checked at this time, on the progress-status display unit C12, the partial region P11 corresponding to the head region is displayed in a color corresponding to the processing stage F3 (undergoing processing) to indicate the progress status of the processing T2.
(Step S13c, Step S22c)

When the processing of the head region medical image Sr11 is complete, the image processor 123 of the execution environment 12c outputs the post-processing head region medical image Sr11 to the progress managing unit 13. Moreover, the progress managing unit 13 identifies the time at which the post-processing head region medical image Sr11 is received from the image processor 123 as the end time. The progress managing unit 13 inputs the identified end time into the end-time information E14 of the row R2a in the progress information D121 appended to the post-processing head region medical image Sr11. As a result, the progress managing unit 13 recognizes that the progress of the processing performed by the operator Uc on the head region medical image Sr11 has transitioned from the processing stage F3 (undergoing processing) to the processing stage F4 (processing complete). The progress managing unit 13 stores the head region medical image Sr11 in the image storage 11. Moreover, the image processor 123 outputs the results of the processing performed on the head region medical image Sr11 to the UI controller 121. The UI controller 121 displays the acquired processing results on the client 2c (Step S13c). As a result, the results of the processing T2 are displayed on the client 2c operated by the operator Uc (Step S22c). If the progress status is checked at this time, on the progress-status display unit C12, the partial region P11 corresponding to the head region is displayed in a color corresponding to the processing stage F4 (processing complete) to indicate the progress status of the processing T2.

(Step S14, Step S02)

Here, we shall refer to FIG. 6. From among the series-specific medical images corresponding to the study St1, the progress managing unit 13 confirms the progress information of medical images for which processing has been requested. If the processing is complete for all of the medical images for which processing has been requested, the progress managing unit 13 reads out the user information of the operator Ua, who is the request source associated with the progress information D121. The progress managing unit 13 identifies the execution environment 12a corresponding to the operator Ua based on the user information, and notifies the execution environment 12a that the processing requested for the medical images related to the study St1 have been completed (Step S14). As a result, the completion of the requested processing is notified on the client 2a that is operated by the operator Ua (Step S02).

Figure 10:
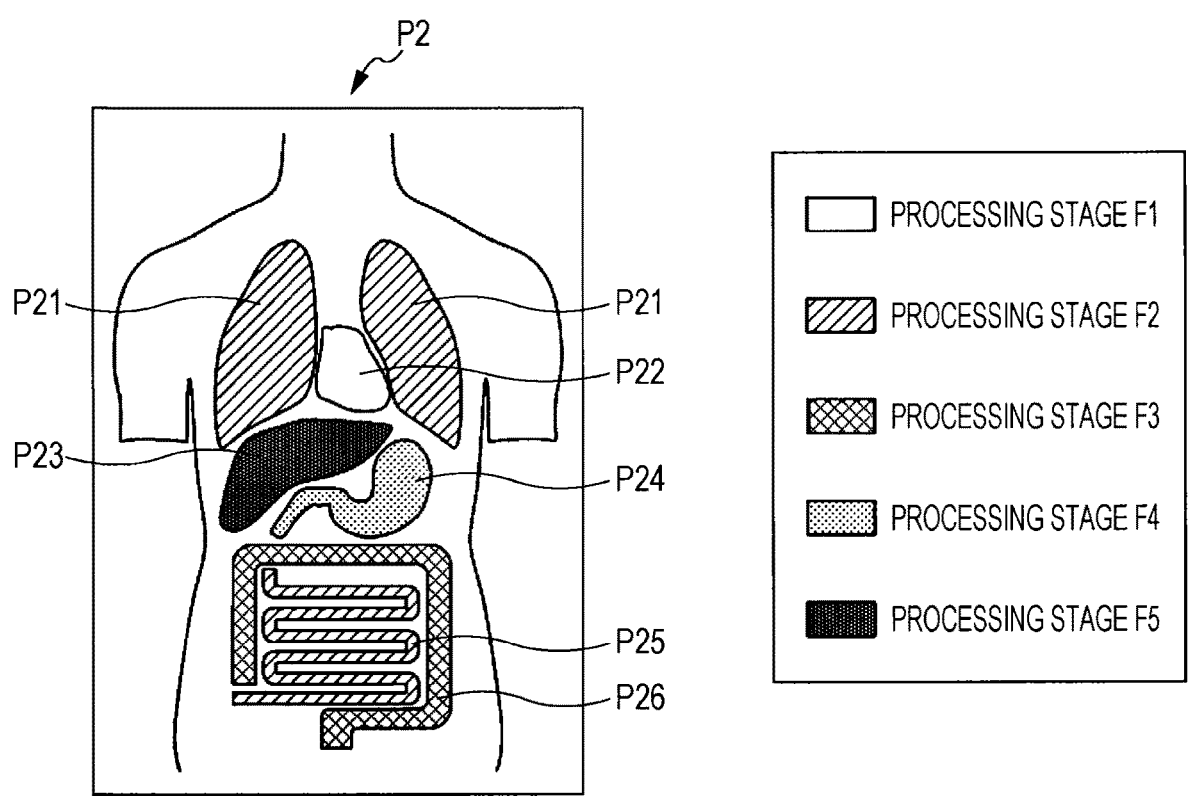
FIG. 10 shows an example of an operation screen of the medical image processing system according to the present embodiment.

In the above, as shown in FIG. 5, examples have been described in which the progress status is displayed for individual body regions such as the head region, the arms, and the abdominal region, but the units used for displaying the progress status as well as the display mode may be changed as needed in accordance with the operations being performed. FIG. 10 shows one mode of a screen displayed on the progress-status display unit C12. FIG. 10 shows the display region P2, which resembles the interior of the chest region and the abdominal region. The display region P2 is configured by including the partial regions P21-P26 that correspond to each organ. The partial regions P21-P26 are associated by the progress-screen generator 122 with the medical images of each series corresponding to the study selected in the study-list display unit C11. For example, the partial region P21 corresponds to the lungs and is associated with medical images of the lungs. Similarly, the partial region P22 is associated with the heart, the partial region P23 with the liver, the partial region P24 with the stomach, the partial region P25 with the small intestine, and the partial region P26 with the large intestine. Moreover, the partial regions P21-P26 are color-coded and displayed as shown in FIG. 10 by the progress-screen generator 122 in accordance with the progress status of processing performed on the associated medical images. The data management methods and the details of processing accompanying display are the same as those for the display region P1 shown in FIG. 5.

Moreover, the display regions P1 and P2 may be used in combination. For example, the partial regions P12 and P13 of the display region P1 shown in FIG. 5 may be associated in advance with the display region P2 shown in FIG. 10, and when the partial region P12 or P13 is selected, the display region P2 may be displayed. In this case, operations may be performed to change the display modes of the partial regions P12 and P13 in accordance with the progress status of processing performed on each medical image associated with each of the partial regions P21-P25.

As described above, according to the medical image processing system of the present embodiment, even when multiple operators perform sequential processing on a single medical image, it becomes possible to display the progress status of the processing performed on each medical image on a screen based on the appended progress information.

A number of embodiments have been explained; however, these embodiments provide examples and are not intended to limit the scope of the invention. It is possible for these novel embodiments to be carried out in various other forms of embodiments, making it possible to allow for various omissions, replacements, and changes without departing from the scope of the invention. These embodiments and variations thereof are included in the scope and spirit of the invention and are also included in the equivalent scope described in the scope of the claims.

EXPLANATION OF THE SYMBOLS

1: Server
11: Image storage
12a, 12b, 12c: Execution environment
121: UI controller
122: Progress-screen generator
123: Image processor
13: Progress managing unit
14: Display data storage
15: User information storage
2a, 2b, 2c: Client

What is claimed is:

1. A medical image processing system comprising:
a plurality of clients;
a server; and
a medical imaging device to capture medical images of a subject; wherein
the clients are each configured to request corresponding one of a plurality of image processors of the server to perform image processing on at least one of a plurality of the medical images of different body regions of a single subject, and
the server comprises:
an image storage to store the medical images of the subject captured by the medical imaging device;
the image processors each corresponding to one of the clients, the image processors configured to, in response to a request regarding a medical image of a body region from their respective clients, perform processing on the medical image;
a processor configured to:
associate the medical images to store the medical images in the image storage in a readable/writable manner in advance;
when a specific one of the image processors receives a request regarding a specific medical image from a corresponding one of the clients, read the specific medical image out of the image storage to transmit the specific medical image to the specific image processor so that processing required by the corresponding one of the client is performed on the specific medical image, and after the processing, write the specific medical image into the image storage;

based on a process of writing to and reading from the image storage, determine one of a plurality of stages to which progress of the processing on the specific medical image belongs, and associate the one of the stages with the specific image processor and the specific medical image to thereby create progress information, the stages including a stage where the specific medical image is unprocessed, a stage where the specific medical image is being processed, and a stage where the processing is completed; and a UI controller configured to display a plurality of screen regions each corresponding to one of the body regions, to create display screen data for visually providing the stages of the progress of the processing in one of the screen regions corresponding to the specific medical image, and to send the display screen data to the corresponding one of the clients.

2. The medical image processing system according to claim 1, wherein when the processor causes another image processor to perform processing on the specific medical image, which has been processed by the specific image processor, in response to a request for processing regarding the specific medical image from another client, the processor creates progress information that indicates progress of the processing performed by the other image processor based on a process of writing to and reading from the image storage for the processing by the other image processor, and the UI controller is configured to create display screen data indicating the progress of the processing performed by each of the image processors in a list based on the progress information for the specific image processor and the other image processor, and send the display screen data to the corresponding one of the clients.

3. The medical image processing system according to claim 1, wherein the processor is configured to manage processing history of each of the medical images from when the medical image is stored first until after the medical image is processed in response to a request in association with the medical image, and in response to a designation of one of the screen regions, the UI controller creates history screen data based on the processing history associated with a medical image of a body region corresponding to the screen region, and sends the history screen data to the corresponding one of the clients.

* * * * *